United States Patent [19]

Wolfrom et al.

[11] 4,326,523

[45] Apr. 27, 1982

[54] METHOD OF SUPPLYING MICRONUTRIENTS TO ANIMALS

[75] Inventors: Glen W. Wolfrom; Robert D. Williams, both of Terre Haute, Ind.; Herbert T. Peeler, Northbrook, Ill.; Richard E. Ivy, Terre Haute, Ind.

[73] Assignee: International Minerals & Chemical Corp., Terre Haute, Ind.

[21] Appl. No.: 180,798

[22] Filed: Aug. 25, 1980

[51] Int. Cl.$^3$ .............................................. A61M 7/00
[52] U.S. Cl. .................................... 128/260; 424/19; 424/131
[58] Field of Search ............... 128/260, 222, 223, 264, 128/271; 424/19, 31-37, 131, 134, 140, 143, 144, 145, 147, 150

[56] References Cited

U.S. PATENT DOCUMENTS

| | | | |
|---|---|---|---|
| 3,491,187 | 1/1970 | Ely | 424/181 |
| 3,499,445 | 3/1970 | Reed | 128/260 |
| 3,952,036 | 4/1974 | Suh | 260/439 |
| 3,975,513 | 8/1976 | Hecht et al. | 424/19 |
| 3,991,750 | 11/1976 | Vickery | 128/260 |
| 4,067,994 | 1/1978 | Anderson et al. | 424/295 |
| 4,191,741 | 3/1980 | Hudson et al. | 128/260 |
| 4,220,153 | 9/1980 | Dresback | 128/260 |
| 4,230,686 | 10/1980 | Schopflin et al. | 128/260 |

OTHER PUBLICATIONS

Merck Index, 9th Ed., 1976, pp. 1287–1288.
Ackerman, L.J., et al: Transmissible Gastroenteritis in Three-Week-Old Pigs, Am. J. Vet. Res. 33(1):115–120, 1972.
Furugouri, K.: Plasma Iron and Total Iron-Binding Capacity in Piglets etc., J. Animal Science 34(3):421-426, 1972.
Danielson, D.M., et al: Supplemental Iron for the Artificially Reared Piglet, J. Animal Science 40(4):621–623, 1975.
Thoren-Tolling, K. et al: Cellular Distribution of Orally and Intramuscularly Administered Iron Dextran in Newborn Piglets, Canadian J. comp. Med. 41:318–325, 1977.
Webster, W.R. et al: Evaluation of Oral Iron Galactan as a Method of Iron Supplementation for Intensively Housed Sucking Piglets, Australian Veterinary Journal 54:345–348, 1978.
Brady, P.S. et al: Evaluation of an Amino Acid-Iron Chelate Hematinic for the Baby Pig, J. Animal Sci. 47(5):1135-40, 1978.
Tait, R.M. et al: Response of Newborn Lambs to Iron--Dextran Injection, Can. J. Animal Science 59:809–811, 1979.
Abstracts, Animal Nutrition and Health, Jan.-Feb., 1980, p. 10.
Johnson, C.M.: Selenium in the Environment, Residue Reviews 62:102, 1976.
Cunha, T.J.: The Value of Feeding Selenium, Feedstuffs, May 21, 1973, p. 48.
*Mollerberg, et al: Acta Vet. Scand. 16:197, 1975.

*Primary Examiner*—C. Fred Rosenbaum
*Attorney, Agent, or Firm*—H. J. Barnett

[57] ABSTRACT

A method of administering micronutrients to animals over extended periods by subcutaneous implant. Important micronutrients, including iron, copper, selenium, zinc, manganese, cobalt, molybdenum, chromium, silicon, iodine, biotin, vitamins E and $B_{12}$ are supplied conveniently, and in positive, predetermined amounts by means of subcutaneously implanted pellets containing the micronutrient and a suitable excipient to provide controlled release of the micronutrient over an extended period of time. One example comprises iron dextran in combination with a lactose, fibrin, or other suitable excipient, in the form of a pellet which is subcutaneously implanted behind the ear of piglets to supply sufficient iron for optimum growth and to avoid iron-deficiency anemia. Important trace elements which may also be administered in carefully controlled amounts in suitable salt forms by the method of this invention include nickel, tin, vanadium, fluorine and arsenic.

16 Claims, No Drawings

METHOD OF SUPPLYING MICRONUTRIENTS TO ANIMALS

BACKGROUND OF THE INVENTION

The importance of micronutrients in animal diets is well documented. Piglets usually suffer from iron deficiency, and various methods of administering supplemental iron have been described, including oral feeding (U.S. Pat. Nos. 3,491,187 and 4,067,994); parenteral administration (injection) or slow release tablets (U.S. Pat. Nos. 3,952,036 and 3,975,513).

A substantial amount of information has been published documenting various forms of iron employed to treat anemia in newborn piglets:

| Author(s) | Title | Reference |
| --- | --- | --- |
| Ackerman, et al | Transmissible Gastroenteritis in Three-Week-Old Pigs: Study of Anemia and Iron Absorption | Am. J. Vet. Res., Vol. 33, No. 1 (January 1972) |
| Furugouri, K. | Plasma Iron and Total Iron-Binding Capacity in Piglets in Anemia and Iron Administration | J. of Animal Science, Vol. 34, No. 3, 1972 |
| Danielson, et al | Supplemental Iron for the Artificially Reared Piglet | J. of Animal Science, Vol. 40, No. 4, 1975 |
| Thoren-Tolling et al | Cellular Distribution of Orally and Intramuscularly Administered Iron Dextran in Newborn Piglets | Can. J. Comp. Med., Volume 41, 1977 |
| Webster, et al | Evaluation of Oral Iron Galactan as a Method of Iron Supplementation for Intensively Housed Suckling Piglets | Australian Vet. J., Volume 54, 1978 |
| Brady, et al | Evaluation of an Amino Acid-Iron Chelate Hematinic for the Baby Pig | J. of Animal Science, Volume 47, No. 5, 1978 |

In the past, iron has been administered to piglets primarily as an oral feed or by parenteral injection. In the case of injections, it has been necessary to repeat the procedure more than once during the growing period of the piglets, with resultant stress, plus extra handling, which adds to the cost of meat production. Administration as an oral feed is inherently uncertain. Some piglets may receive excess iron while others in the litter may not receive enough to prevent iron deficiency anemia.

It has been reported in the literature that anemia can also occur in rapidly growing lambs under intensive systems of management. Iron-dextran injections were used to combat the problem. See: Notes, Canadian Journal of Animal Science 59:809–811, December 1979. Subcutaneous implanting of iron dextran in lambs was not suggested.

SEA's Livestock Insects Laboratories (USDA) in Beltsville, Md., and Kerrville, Tex., have reported that grubs emerging from infested calves can be controlled by the use of ear-implanted pellets which release minute amounts of experimental compounds. Compounds are reported to be under development which will be effective against bloodsucking insects and ticks in very low dose levels in an animal's blood stream. See: Animal Nutrition and Health/January-February 1980, "Abstracts", page 10.

Selenium (Se) is added to many poultry feeds, turkey feed in particular, to avoid selenium deficiency diseases. The addition of selenium to feeds for swine, sheep, cattle and chickens (0.1 ppm) and for turkeys (0.2 ppm) has been approved by FDA (21 CFR 573.920; Federal Register 44(9):5342, 1979. Implanting of poultry to supply micronutrients in a slow-release mode has not been suggested until now, however.

Selenium deficiency has been reported to be associated with nutritional muscular dystrophy (white-muscle disease, WMD) in lambs, calves and foals, and other diseases in poultry and swine. See: Johnson, C. M., "Selenium in the Environment", Residue Reviews 62:102(1976); Cunha, T. J., "The Value of Feeding Selenium", Feedstuffs, May 21, 1973, page 48. At present, the only known commercial treatment for selenium deficient young lambs is subcutaneous or intramuscular injection of an oil-based, sodium selenite-containing compound.

Young calves have been treated with micronutrients including iron, zinc, manganese and selenium. Treating veal calves with injections of iron dextran is described in: Mollerberg et al, 1975, Acta Vet. Scand. 16:197, cited by Church, D. C. et al 1979, Digestive Physiology and Nutrition of Ruminants, Volume 2, O&B Books, Inc. Corvallis, Oreg., page 130.

SUMMARY

This invention provides a positive and reliable method of administering important micronutrients to animals over extended periods by means of slow release pellets containing one or more of the required micronutrients. The pellets in the required dosage are subcutaneously implanted on the animal, and gradually release the micronutrients directly into the animal's circulatory system over extended periods of time.

This method of administering micronutrients is particularly well-suited to providing dietary iron to fast-growing animals such as piglets, lambs, dairy and beef calves, which are susceptible to iron-deficiency anemia. Selenium is added to many poultry feeds, and is particularly important in the diets of turkeys. Supplying micronutrients such as selenium by subcutaneous implant insures each bird will receive the required amount. Other micronutrients which may be administered in the same way include: certain salt forms of copper, zinc, manganese, cobalt, molybdenum, iodine, and vitamins such as biotin, E and $B_{12}$. Trace elements including nickel, tin, vanadium, fluorine and arsenic in suitable salt forms may also be administered by this method when a requirement for these exists due to special circumstances.

The implant method of the invention is convenient, and supplies premeasured amounts of the micronutrients in a gradual, slow release form over an extended period of time. The pellets include the micronutrient in a suitable form in combination with a biocompatible, absorbable excipient such as lactose, fibrin, methylcellulose, collagen, cholesterol, carbowax, beeswax, dibutylphthalate (DBP), polyvinylpyrrolidone (PVP), zinc stearate, polylactides including α-hydroxypropionic acid, polyethylene glycol (PEG), sugar-starch combinations, and suitable combinations of the above. Release time may be extended as desired. Certain silicone-based materials containing the desired micronutrients may also be used as removable implants so that supply of the active material may be terminated abruptly when this is desired.

DETAILED DESCRIPTION

The following examples are provided to show how the method can be applied for specific micronutrients. Other specific applications are included within the scope of the invention, and will be suggested by the following examples.

EXAMPLE 1

Baby pigs three to five days of age (thirty-five piglets) were assigned to three treatments: no iron, injectable iron dextran (100 mg iron/pig) and iron dextran implants (94.2 mg iron/pig). Blood samples were taken initially and two weeks later to determine changes in hematocrit and hemoglobin. The piglets were weighed initially and at weekly intervals for an additional three weeks. The object of the test was to determine the effectiveness of iron implants as measured by changes in blood hemoglobin and hematocrit levels. The implant pellet composition is set forth below:

| Ingredients | Amounts (mg per implant pellet) |
| --- | --- |
| Iron dextran[1] | 41 |
| Fibrin (excipient)[2] | 19 |
| Boric acid | 1.1 |
| Magnesium stearate | 0.5 |
| Total | 61.6 |
| Iron content per implant pellet | 15.7 |

(Number of implant pellets/piglet was 6, to provide 94.2 mg)
[1]Prepared from iron dextran complex obtained from Med-Tech, Inc., Elwood, Kansas 66024
[2]Fibrin obtained from ICN Pharmaceuticals, Inc., Plainview, New York Piglets receiving injectable iron were given 1 ml of injectable iron dextran (obtained from Med-Tech, Inc., Elwood, Kans. 60024) intramuscularly in the neck providing 100 mg iron. The iron dextran implants were in the form of six pellets implanted subcutaneously behind the right ear of each piglet in this test group to provide a total of 94.2 mg iron. Table 1 below shows the comparison of the implant iron treatment compared to injection treatment and a control group which received no iron.

TABLE 1

| | Treatment Groups | | |
| --- | --- | --- | --- |
| Observed Results | No Iron (10 pigs) | Injectable Iron Dextran (12 pigs) | Iron Dextran Implants (13 pigs) |
| Hemacrit (% PCV) | 26.0 | 35.1 | 34.5 |
| Hemoglobin (g/dl) | 8.1 | 11.2 | 10.5 |
| Body Weight (g) | 5484 | 5427 | 5966 |

All pigs nursed their dams throughout the testing period. No supplemental feed was given to the baby pigs, but they did have access to their dam's feed and water. As shown in the above table, the hemoglobin concentration for implanted iron was greater than the controls, and the implanted iron was utilized as effectively as injected iron in eliciting hematocrit and hemoglobin responses. The above example shows that subcutaneous implanting of micronutrients such as iron is a viable alternative to injecting such materials. The amount of iron dextran supplied by implant in the above tests was about 6% by weight less than was supplied by injection. It is expected that the results can be made even more favorable for implants with an increased dosage level per pellet.

EXAMPLE 2

Another test was conducted in baby pigs, comparing two iron dextran injection procedures with two different implant pellet procedures. In this comparison, fifty randomly selected baby pigs (three to five days old) were assigned to four test groups as follows:

Group I (15 pigs) initially given 1.0 ml intramuscular injection of liquid iron dextran and same treatment repeated two weeks later.

Group II (13 pigs) initially given 2.0 ml injection of liquid iron dextran.

Group III (12 pigs) iron dextran implant pellets employing fibrin excipient.

Group IV (10 pigs) iron dextran implant pellets employing lactose excipient.

In this test, changes in body weight, blood hemoglobin and hematocrit values were determined four weeks following initiation of the treatments. Each 1.0 ml of injectable iron contained 100 mg of elemental iron, providing 200 mg elemental iron for pigs in Groups I and II, since all these pigs received a total of 2 ml of injected iron dextran. The implanted pigs received precipitated iron dextran in the form of subcutaneously implanted pellets as follows: Group III, 203 mg elemental iron, and Group IV, 190 mg elemental iron.

The implant pellets used in this test had the following compositions:

| | Composition (mg per implant) | |
| --- | --- | --- |
| Ingredient | Group III | Group IV |
| Precipitated iron dextran | 41.0 | 41.0 |
| Fibrin | 19.0 | |
| Lactose | | 19.0 |
| Boric acid | 1.1 | 1.1 |
| Magnesium stearate | 0.5 | 0.5 |
| Iron content (analyzed) | 16.9 | 15.8 |
| Total iron per pig (12 implants each pig) | 202.8 | 189.6 |

Pellet Manufacture Procedure

The precipitated iron dextran was prepared by adding an equal volume of methanol to an injectable iron dextran (from Med-Tech, Inc., Elwood, Kans.). The mixture is stirred, centrifuged and the supernatant is discarded. The material remaining is air-dried and ground prior to pelleting. The pellets weighed about 61.6 mg each and were about one-eighth inch in diameter, and had a Strong Cobb Hardness of about 10. The pellets were made by thoroughly blending the ingredients and then pelleting the blended ingredients in a Model B-2 Stokes Rotary Tableting Machine using a cylindrical die insert to form cylindrical pellets. The pellets were then subcutaneously implanted behind the ears of the test animals. The results observed in the subject tests indicated that lactose and fibrin perform satisfactorily in implant pellet formulations to permit the controlled slow release of micronutrients, such as iron dextran. Hematocrit response and blood hemoglobin level for the two implant pellet groups (III and IV) were comparable to the Group II iron dextran injected pigs.

EXAMPLE 3

Laboratory rats were tested to determine whether administration of iron by means of subcutaneously implanted pellets is as effective as dietary iron to restore hematocrit and hemoglobin level of the test animal's blood. A total of 48 animals, Cox SD male rats, age 21 days were used in this test, which lasted 42 days. The rats were randomly allotted to eight treatment groups of six rats as shown below in Table 2.

TABLE 2

| Group (6 rats) | Treatment |
| --- | --- |
| 1 | Added dietary iron (0 ppm); placebo implant |
| 2 | Added dietary iron (3.5 ppm); placebo implant |
| 3 | Added dietary iron (15.3 ppm); placebo implant |
| 4 | Iron deficient diet; precipitated iron dextran implant (10.8% Fe) |
| 5 | Iron deficient diet; ferrous chloride implant (12.2% Fe) |
| 6 | Iron deficient diet; ferrous fumarate implant (12.9% Fe) |
| 7 | Iron deficient diet; ferrous sulfate implant (11.6% Fe) |
| 8 | Iron deficient diet; reduced electrolytic iron implant (12.8% Fe) |

The above test animals were then placed on a meal type iron deficient diet (7.5 ppm Fe) and deionized water ad libitum. After four weeks of the above diet, the animals were bled to determine hematocrit (PCV) and hemoglobin (Hb) levels. Treatments were then begun according to Table 2. Groups 2 and 3 received iron in the form of ferrous sulfate heptahydrate. The Groups 1–3 animals also received placebo implants containing no iron. The animals in Groups 4–8 continued to receive the iron deficient diet in addition to the indicated implants containing specific forms of iron.

Each implant pellet weighed about 61.6 mg, was one-eighth inch in diameter and was compressed to about 5 SCHU. The pellets were implanted subcutaneously in the mid-scapular region of the test animals. Each implant was formulated to provide approximately eight mg of iron per test animal. The compositions of the implant pellets are set forth below in Table 2-A.

TABLE 2-A

| | Composition of Implants | | | | | |
| --- | --- | --- | --- | --- | --- | --- |
| Ingredients | Iron Dextran | Ferrous Chloride | Ferrous Fumarate | Ferrous Sulfate | Reduced Iron | Placebo |
| Iron source | 18.2 | 18.2 | 24.2 | 22.2 | 8.3 | 0 |
| Fibrin | 20.0 | 20.0 | 20.0 | 20.0 | 20.0 | 20.0 |
| Lactose | 21.8 | 21.8 | 15.8 | 17.8 | 31.7 | 40.0 |
| Boric acid | 1.1 | 1.1 | 1.1 | 1.1 | 1.1 | 1.1 |
| Magnesium stearate | 0.5 | 0.5 | 0.5 | 0.5 | 0.5 | 0.5 |

The iron deficient diet composition is set forth below in Table 2-B.

TABLE 2-B

| Composition of Iron-Deficient Diet | |
| --- | --- |
| Ingredient | Per cent |
| Glucose | 50.25 |
| Corn starch | 15.00 |
| Vitamin-free casein | 20.00 |
| Gelatin | 5.00 |
| Corn oil | 5.00 |
| AIN mineral premix (no iron) | 3.50 |
| AIN vitamin premix | 1.00 |

TABLE 2-B-continued

| Composition of Iron-Deficient Diet | |
| --- | --- |
| Ingredient | Per cent |
| Choline chloride | 0.15 |
| dl-Methionine | 0.15 |

The above diet was obtained from Zeigler Bros., Inc., P.O. Box 95, Gardners, Pa. 17324. The above AIN mineral and vitamin premixes are further described in the Journal of Nutrition 107:1340 (1977).

A two-week repletion period following administration of treatments, after which blood samples were again taken for determination of PCV and Hb. The efficacy of the particular treatment was evaluated by the relative increase in PCV and Hb levels of the blood during the repletion period.

Comparison of the test results in all groups showed that iron dextran administered in the form of implants was just as effective as dietary iron in restoring the hematocrit and hemoglobin level of blood in the test animals.

EXAMPLE 4

When Example 1 is repeated, with newborn lambs instead of piglets, and with the dosage adjusted as necessary for the size of the lambs, the results of this test are expected to be in agreement with the results obtained with newborn pigs. It can be concluded that subcutaneous implanting of iron dextran pellets is a viable alternative for supplying dietary iron to newborn lambs.

EXAMPLE 5

When Example 1 is repeated, with newborn calves instead of piglets, and with the dosage adjusted for the relatively larger size of the calves, the results are expected to be in agreement with the results obtained using newborn pigs. Subcutaneous implanting of iron dextran pellets is a viable alternative for supplying dietary iron to newborn calves. Other micronutrients, including zinc, manganese, selenium, copper, cobalt, molybdenum, chromium, silicon, iodine, biotin, vitamins E and $B_{12}$ may also be supplied to bovine animals in this same way.

EXAMPLE 6

A test group of selenium deficient lambs (2 weeks of age) can be implanted with pellets containing sodium selenite in an absorbable formulation to provide a minimum of 3.3 mg of selenium during the critical first eight weeks. This group of lambs is compared to a second group receiving two 1 ml injections of selenium containing a total of 2 mg selenium during the first eight week test period, both test groups also receiving vitamin E. Tests of the lambs will show that both test groups recover from the initial selenium deficiency, and neither group shows any symptoms of nutritional muscular dystrophy which was evident in another group of lambs which were continued on a selenium deficient diet for an eight week test period. The above results show that trace minerals, such as selenium, can be effectively supplied by subcutaneous implant as a viable alternative to intramuscular injection.

Other possible compounds which can be incorporated into implant pellets to administer the various micronutrients to the host animal are listed below.

Iron may also be in the form of ferric hydroxide. Iron dextran is the presently preferred form of iron for implant pellets, however.

Copper may be in the form of cupric sulfate; cupric sulfate, pentahydrate; cupric acetate; cupric butyrate; cupric citrate; cupric glycinate; cupric selenate; cupric selenide; cupric selenite; cupric tartrate; and cuprous selenide.

In addition to sodium selenite, selenium may be in the form of sodium selenate, potassium selenide, potassium selenite, calcium selenate, magnesium selenate, magnesium selenite, manganese selenide, cupric selenate, cupric selenide, cupric selenite, cuprous selenide and zinc selenate.

Cobalt can be delivered in the form of cobaltic acetate, cobaltous acetate, cobaltous iodide, cobaltous oxalate, cobaltous sulfate.

Molybdenum can be in the form of molybdenum sesquioxide, sodium molybdate (VI), potassium molybdate (VI), sodium molybdate dihydrate and sodium molybdate pentahydrate.

Chromium compounds useful in the method of this invention include: chromic acetate, chromic potassium oxalate, chromic potassium sulfate and chromic sulfate. Silicon may take the form of sodium metasilicate and potassium metasilicate.

Possible compounds to provide zinc include zinc acetate, zinc chromate (VI) hydroxide, zinc citrate, zinc dichromate (VI), zinc iodate, zinc iodide, zinc lactate, zinc perchlorate, zinc selenate, zinc selenide and zinc sulfate.

Manganese may be administered in pellet form as manganese acetate; manganese iodide; and manganese sulfate.

Iodine compounds expected to be administered by pellet include manganese iodide, zinc iodide, zinc iodate, cuprous iodide, cobaltous iodide, ferrous iodide, iodine colloidal, potassium iodide, potassium iodate, calcium iodide, sodium iodate and sodium iodide.

Vitamin E can be administered as α-tocopherol, β-tocopherol, γ-tocopherol, δ-tocopherol, α-tocopheryl acetate, α-tocopherol acetate, either in pure form or in mixtures. The d-form of α tocopherol acetate and racemic mixtures of dl-α-tocopherol acetate are presently preferred. Vitamin $B_{12}$ is conveniently administered in the form of cyanocobalamin with a suitable diluent, and can be mixed with a suitable excipient and pelleted for slow release as needed.

In each case, the dosage level of the particular micronutrient is adjusted to provide the appropriate amount of the micronutrient over the required time period. In some applications, multiple pellet implants will be required to provide enough micronutrient to the host animal.

We claim:

1. A method of supplying a micronutrient to meat-producing animals comprising formulating the micronutrient in a slow release, absorbable pellet in combination with a biocompatible, absorbable carrier, and subcutaneously implanting said pellet in a meat-producing animal to thereby slowly release said micronutrient directly into the animal's circulatory system as said pellet is absorbed, said micronutrient being selected from the group consisting of suitable compositions containing iron, copper, selenium, zinc, manganese, iodine, cobalt, molybdenum, chromium, silicon, biotin, vitamin E and vitamin $B_{12}$, and said absorbable carrier being selected from the group consisting of lactose, fibrin, methylcellulose, collagen, cholesterol, carbowax, beeswax, dibutylphthalate (DBP), polyvinylpyrolidone (PVP), zinc stearate, polyactides including α-hydroxypropionic acid, polyethylene glycol (PEG), sugar-starch combinations and suitable combinations of the above.

2. The method of claim 1 in which the micronutrient comprises iron in the form of iron dextran, and the meat-producing animal which is implanted with said absorbable pellet is selected from the group consisting of baby pigs, lambs, dairy calves and beef calves.

3. The method of claim 1, in which the micronutrient is copper in the form of one or more compounds of copper selected from the group consisting of cupric sulfate; cupric sulfate, pentahydrate; cupric acetate; cupric butyrate; cupric citrate; cupric glycinate; cupric selanate; cupric selenide; cupric tartrate; and cuprous selenide.

4. The method of claim 1, in which the micronutrient is selenium in the form of one or more compounds of selenium selected from the group consisting of sodium selenite, sodium selenate, potassium selenide, potassium selenate, calcium selenate, calcium selenide, magnesium selenate, magnesium selenite, manganese selenide, cupric selenate, cupric selenide, cupric selenite, cuprous selenide and zinc selenate.

5. The method of claim 1, in which the micronutrient is cobalt in the form of one or more compounds selected from the group consisting of cobaltic acetate, cobaltous acetate, cobaltous iodide, cobaltous oxalate and cobaltous sulfate.

6. The method of claim 1, in which the micronutrient is molybdenum in the form of one or more compounds selected from the group consisting of molybdenum sesquioxide, sodium molybdate (VI), potassium molybdate (VI), sodium molybdate dihydrate and sodium molybdate pentahydrate.

7. The method of claim 1, in which the micronutrient is chromium in the form of one or more compounds selected from the group consisting of chromic acetate, chromic potassium oxalate, chromic potassium sulfate and chromic sulfate.

8. The method of claim 1, in which the micronutrient is silicon in the form of one or more compounds selected from the group consisting of sodium metasilicate, potassium silicate and combinations thereof.

9. The method of supplying a trace element to animals comprising formulating the trace element in a slow release pellet in combination with a biocompatible carrier, and subcutaneously implanting said pellet in an animal to thereby slowly release said trace element directly into said animal's circulatory system, said trace element being selected from the group consisting of nickel, tin, vanadium fluorine and arsenic in suitable salt forms, and combinations thereof.

10. The method of claim 1, in which the micronutrient is zinc in the form of one or more compounds of zinc selected from the group consisting of zinc acetate, zinc chromate (VI) hydroxide, zinc citrate, zinc dichromate (VI), zinc iodate, zinc iodide, zinc lactate, zinc perchlorate, zinc selenate, zinc selenide and zinc sulfate.

11. The method of claim 1, in which the micronutrient is manganese in the form of one or more compounds selected from the group consisting of manganese acetate; manganese iodide; and manganese sulfate.

12. The method of claim 1, in which the micronutrient is iodine in the form of one or more compounds selected from the group consisting of manganese iodide, zinc iodide, zinc iodate, cuprous iodide, cobaltous iodide, ferrous iodide, iodine colloidal, potassium iodide, potassium iodate, calcium iodide, sodium iodate and sodium iodide.

13. The method of claim 1, in which the pellet includes biotin.

14. The method of claim 1, in which the pellet includes Vitamin E in the form selected from the group consisting of α-tocopherol, β-tocopherol, γ-tocopherol, δ-tocopherol, α-tocopheryl acetate, dl-α-tocopherol acetate, and combinations thereof.

15. The method of claim 1, in which the pellet includes Vitamin $B_{12}$ in the form of cyanocobalamin.

16. An absorbable implant pellet for supplying micronutrients to a host animal when said pellet is subcutaneously implanted in said host animal, said pellet comprising a biocompatible, absorbable carrier selected from the group consisting of lactose, fibrin, methylcellulose, collagen, cholesterol, carbowax, beeswax, dibutylphthalate (DBP), polyvinylpyrolidone (PVP), zinc stearate, polylactides including α-hydroxypropionic acid, polyethylene glycol (PEG), sugar-starch combinations, silicon-based materials, and suitable combinations of the above and one or more micronutrients in the form of one or more compounds selected from the group consisting of precipitated iron dextran; ferric hydroxide; cupric sulfate; cupric sulfate, pentahydrate; cupric acetate; cupric butyrate; cupric citrate; cupric glycinate; cupric selenate; cupric selenide; cupric tartrate; cuprous selenide; sodium selenite; sodium selenate; potassium selenide; potassium selenate; calcium selenate; calcium selenide; magnesium selenate; magnesium selenite; cupric selenate; cupric selenide; cupric selenite; cuprous selenide; zinc selenate; cobaltic acetate; cobaltous acetate; cobaltous iodide; cobaltous oxalate; cobaltous sulfate; molybdenum sesquioxide; sodium molybdate (VI); potassium molybdate (VI); sodium molybdate dihydrate; sodium molybdate pentahydrate; chromic acetate; chromic potassium oxalate; chromic potassium sulfate; chromic sulfate; sodium metasilicate; potassium silicate; zinc acetate; zinc chromate (VI) hydroxide; zinc citrate; zinc dichromate (VI); zinc iodate; zinc iodide; zinc lactate; zinc perchlorate; zinc selenate; zinc selenide; zinc sulfate; manganese acetate; manganese iodide; manganese sulfate; manganese iodide; zinc iodode; zinc iodate; cuprous iodide; cobaltous iodide; ferrous iodide; iodine colloidal; potassium iodide; potassium iodate; calcium iodide; sodium iodate; sodium iodide; biotin; α-tocopherol, β-tocopherol, γ-tocopherol, δ-tocopherol, α-tocopheryl acetate, α-tocopherol acetate, dl-α-tocopherol acetate, cyanocobalamin and mixtures thereof.

* * * * *

UNITED STATES PATENT AND TRADEMARK OFFICE
CERTIFICATE OF CORRECTION

PATENT NO. : 4,326,523
DATED : April 27, 1982
INVENTOR(S) : Glen W. Wolfrom et al It is certified that error appears in the above-identified patent and that said Letters Patent are hereby corrected as shown below:

Column 2, line 18, "yound" should read -- young --

Column 7, line 11, "selenite" should read -- selenate --

Column 8, line 3, Claim 1, "polyactides" should read
-- polylactides --

Signed and Sealed this

Third Day of May 1983

[SEAL]

Attest:

Attesting Officer

GERALD J. MOSSINGHOFF
Commissioner of Patents and Trademarks